United States Patent
Pett (10) Patent No.: US 12,274,469 B2
(45) Date of Patent: Apr. 15, 2025

(54) ANGLED INTRAOSSEOUS ACCESS SYSTEM

(71) Applicant: Bard Access Systems, Inc., Salt Lake City, UT (US)

(72) Inventor: Daniel Pett, Sandy, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 857 days.

(21) Appl. No.: 17/410,863

(22) Filed: Aug. 24, 2021

(65) Prior Publication Data

US 2022/0061880 A1    Mar. 3, 2022

Related U.S. Application Data (60) Provisional application No. 63/069,988, filed on Aug. 25, 2020.

(51) Int. Cl.
  *A61B 17/34*  (2006.01)
  *A61B 17/17*  (2006.01)
  *A61B 90/00*  (2016.01)

(52) U.S. Cl.
  CPC .......... *A61B 17/3403* (2013.01); *A61B 17/17* (2013.01); *A61B 17/3472* (2013.01); *A61B 2017/3407* (2013.01); *A61B 2017/3409* (2013.01); *A61B 17/3494* (2013.01); *A61B 2090/034* (2016.02)

(58) Field of Classification Search
  CPC ................ A61B 17/17; A61B 17/3403; A61B 2017/3407; A61B 2017/3409; A61B 17/3472; A61B 17/3494; A61B 2090/034
  See application file for complete search history.

(56) References Cited

U.S. PATENT DOCUMENTS

| | | | |
|---|---|---|---|
| 2,773,501 | A | 12/1956 | Young |
| 3,071,135 | A | 1/1963 | Baldwin et al. |
| 3,261,594 | A | 7/1966 | Michel |
| 3,734,207 | A | 5/1973 | Fishbein |
| 3,753,432 | A | 8/1973 | Guerra |
| 3,804,544 | A | 4/1974 | Adams |

(Continued)

FOREIGN PATENT DOCUMENTS

| CN | 108742795 A | 11/2018 |
|---|---|---|
| CN | 110547847 A | 12/2019 |

(Continued)

OTHER PUBLICATIONS

PCT/US2024/014241 filed Feb. 2, 2024 International Search Report and Written Opinion dated May 8, 2024.

(Continued)

*Primary Examiner* — Larry E Waggle, Jr.
(74) *Attorney, Agent, or Firm* — Rutan & Tucker LLP (57) ABSTRACT

An angled intraosseous access system including a guide block and/or a guide plate is disclosed. The system includes a driver having a body, and including a needle assembly rotatably coupled thereto, the needle assembly defining a needle axis. One of the guide block or the guide plate is configured to engage a skin surface and align the needle assembly axis at a predetermined angle relative to the skin surface to access the medullary cavity at the predetermined angle. Advantageously, the angled needle of the intraosseous access system can mitigate pain during infusion and mitigate backwalling.

22 Claims, 4 Drawing Sheets

(56) References Cited

U.S. PATENT DOCUMENTS

| | | |
|---|---|---|
| 3,811,442 A | 5/1974 | Maroth |
| 3,815,605 A | 6/1974 | Schmidt et al. |
| 3,991,765 A | 11/1976 | Cohen |
| 4,266,555 A | 5/1981 | Jamshidi |
| 4,314,565 A | 2/1982 | Lee |
| 4,342,724 A | 8/1982 | Narra |
| 4,381,777 A | 5/1983 | Garnier |
| 4,383,530 A | 5/1983 | Bruno |
| 4,562,844 A | 1/1986 | Carpenter et al. |
| 4,736,742 A | 4/1988 | Alexson et al. |
| 4,787,893 A | 11/1988 | Villette |
| 4,889,529 A | 12/1989 | Haindl |
| 4,952,207 A | 8/1990 | Lemieux |
| 4,964,854 A | 10/1990 | Luther |
| 4,969,870 A | 11/1990 | Kramer et al. |
| 5,040,542 A | 8/1991 | Gray |
| 5,042,558 A | 8/1991 | Hussey et al. |
| 5,053,017 A | 10/1991 | Chamuel |
| 5,122,114 A | 6/1992 | Miller et al. |
| 5,207,697 A | 5/1993 | Carusillo et al. |
| 5,263,939 A | 11/1993 | Wortrich |
| 5,290,267 A | 3/1994 | Zimmermann |
| 5,312,364 A | 5/1994 | Jacobs |
| 5,332,398 A | 7/1994 | Miller et al. |
| 5,364,367 A | 11/1994 | Banks et al. |
| 5,372,583 A | 12/1994 | Roberts et al. |
| 5,384,103 A | 1/1995 | Miller |
| 5,406,940 A | 4/1995 | Melzer et al. |
| 5,451,210 A | 9/1995 | Kramer et al. |
| 5,554,154 A | 9/1996 | Rosenberg |
| 5,575,780 A | 11/1996 | Saito |
| 5,591,188 A | 1/1997 | Waisman |
| 5,601,559 A | 2/1997 | Melker et al. |
| 5,667,509 A | 9/1997 | Westin |
| 5,688,249 A | 11/1997 | Chang et al. |
| 5,694,019 A | 12/1997 | Uchida et al. |
| 5,779,708 A | 7/1998 | Wu |
| 5,817,052 A | 10/1998 | Johnson et al. |
| 5,853,393 A | 12/1998 | Bogert |
| 5,868,711 A * | 2/1999 | Kramer .............. A61B 17/3472 604/506 |
| 5,885,293 A | 3/1999 | McDevitt |
| 5,927,976 A | 7/1999 | Wu |
| 5,960,797 A | 10/1999 | Kramer et al. |
| 5,967,143 A | 10/1999 | Klappenberger |
| 6,018,227 A | 1/2000 | Kumar et al. |
| 6,056,165 A | 5/2000 | Speranza |
| 6,104,162 A | 8/2000 | Sainsbury et al. |
| 6,117,108 A | 9/2000 | Woehr et al. |
| 6,135,769 A | 10/2000 | Kwan |
| 6,159,161 A | 12/2000 | Hodosh |
| 6,199,664 B1 | 3/2001 | Tkaczyk et al. |
| 6,210,373 B1 | 4/2001 | Allmon |
| 6,228,088 B1 | 5/2001 | Miller et al. |
| 6,247,928 B1 | 6/2001 | Meller et al. |
| 6,270,484 B1 | 8/2001 | Yoon |
| 6,273,715 B1 | 8/2001 | Meller et al. |
| 6,419,490 B1 | 7/2002 | Kitchings Weathers, Jr. |
| 6,458,117 B1 | 10/2002 | Pollins, Sr. |
| 6,527,778 B2 | 3/2003 | Athanasiou et al. |
| 6,547,561 B2 | 4/2003 | Meller et al. |
| 6,602,214 B2 | 8/2003 | Heinz et al. |
| 6,626,887 B1 | 9/2003 | Wu |
| 6,629,959 B2 | 10/2003 | Kuracina et al. |
| 6,641,395 B2 | 11/2003 | Kumar et al. |
| 6,652,490 B2 | 11/2003 | Howell |
| 6,692,471 B2 | 2/2004 | Boudreaux |
| 6,761,726 B1 | 7/2004 | Findlay et al. |
| 6,814,734 B2 | 11/2004 | Chappuis et al. |
| 6,830,562 B2 | 12/2004 | Mogensen et al. |
| 6,875,219 B2 | 4/2005 | Arramon et al. |
| 6,905,486 B2 | 6/2005 | Gibbs |
| 6,916,292 B2 | 7/2005 | Morawski et al. |
| 6,984,213 B2 | 1/2006 | Horner et al. |
| 6,997,907 B2 | 2/2006 | Safabash et al. |
| 7,112,191 B2 | 9/2006 | Daga |
| 7,135,031 B2 | 11/2006 | Flint |
| 7,214,208 B2 | 5/2007 | Vaillancourt et al. |
| 7,347,838 B2 | 3/2008 | Kulli |
| 7,347,840 B2 | 3/2008 | Findlay et al. |
| 7,407,493 B2 | 8/2008 | Cane' |
| 7,458,954 B2 | 12/2008 | Ferguson et al. |
| 7,513,888 B2 | 4/2009 | Sircom et al. |
| 7,530,965 B2 | 5/2009 | Villa et al. |
| 7,534,227 B2 | 5/2009 | Kulli |
| 7,569,033 B2 | 8/2009 | Greene et al. |
| 7,582,102 B2 | 9/2009 | Heinz et al. |
| 7,588,559 B2 | 9/2009 | Aravena et al. |
| 7,658,725 B2 | 2/2010 | Bialecki et al. |
| 7,670,328 B2 | 3/2010 | Miller |
| 7,699,807 B2 | 4/2010 | Faust et al. |
| 7,699,850 B2 | 4/2010 | Miller |
| 7,736,332 B2 | 6/2010 | Carlyon et al. |
| 7,749,225 B2 | 7/2010 | Chappuis et al. |
| 7,798,994 B2 | 9/2010 | Brimhall |
| 7,811,260 B2 | 10/2010 | Miller et al. |
| 7,815,642 B2 | 10/2010 | Miller |
| 7,828,774 B2 | 11/2010 | Harding et al. |
| 7,833,204 B2 | 11/2010 | Picha |
| 7,842,038 B2 | 11/2010 | Haddock et al. |
| 7,850,620 B2 | 12/2010 | Miller et al. |
| 7,850,650 B2 | 12/2010 | Breitweiser |
| D633,199 S | 2/2011 | MacKay et al. |
| 7,899,528 B2 | 3/2011 | Miller et al. |
| 7,905,857 B2 | 3/2011 | Swisher |
| 7,951,089 B2 | 5/2011 | Miller |
| 7,955,297 B2 | 6/2011 | Radmer et al. |
| 7,972,339 B2 | 7/2011 | Nassiri et al. |
| 7,976,502 B2 | 7/2011 | Baid |
| 8,038,038 B2 | 10/2011 | Hillhouse et al. |
| 8,038,664 B2 | 10/2011 | Miller et al. |
| 8,043,253 B2 | 10/2011 | Kraft et al. |
| 8,043,265 B2 | 10/2011 | Abe et al. |
| 8,142,365 B2 | 3/2012 | Miller |
| 8,152,771 B2 | 4/2012 | Mogensen et al. |
| 8,162,904 B2 | 4/2012 | Takano et al. |
| 8,167,899 B2 | 5/2012 | Justis et al. |
| 8,235,945 B2 | 8/2012 | Baid |
| 8,246,584 B2 | 8/2012 | Aravena et al. |
| 8,273,053 B2 | 9/2012 | Saltzstein |
| 8,292,891 B2 | 10/2012 | Browne et al. |
| 8,308,693 B2 | 11/2012 | Miller et al. |
| 8,333,769 B2 | 12/2012 | Browne et al. |
| 8,356,598 B2 | 1/2013 | Rumsey |
| 8,357,163 B2 | 1/2013 | Sidebotham et al. |
| 8,388,541 B2 | 3/2013 | Messerly et al. |
| 8,388,623 B2 | 3/2013 | Browne et al. |
| 8,414,539 B1 | 4/2013 | Kuracina et al. |
| 8,419,683 B2 | 4/2013 | Miller et al. |
| 8,480,632 B2 | 7/2013 | Miller et al. |
| 8,480,672 B2 | 7/2013 | Browne et al. |
| 8,486,027 B2 | 7/2013 | Findlay et al. |
| 8,506,568 B2 | 8/2013 | Miller |
| 8,535,271 B2 | 9/2013 | Fuchs et al. |
| 8,562,615 B2 | 10/2013 | Browne et al. |
| 8,641,715 B2 | 2/2014 | Miller |
| 8,647,257 B2 | 2/2014 | Jansen et al. |
| 8,656,929 B2 | 2/2014 | Miller et al. |
| 8,657,790 B2 | 2/2014 | Tal et al. |
| 8,663,231 B2 | 3/2014 | Browne et al. |
| 8,668,698 B2 | 3/2014 | Miller et al. |
| 8,684,978 B2 | 4/2014 | Miller et al. |
| 8,690,791 B2 | 4/2014 | Miller |
| 8,715,287 B2 | 5/2014 | Miller |
| 8,771,230 B2 | 7/2014 | White et al. |
| 8,781,555 B2 | 7/2014 | Burnside et al. |
| 8,801,663 B2 | 8/2014 | Woehr |
| 8,812,101 B2 | 8/2014 | Miller et al. |
| 8,814,835 B2 | 8/2014 | Baid |
| 8,821,493 B2 | 9/2014 | Anderson |
| 8,828,001 B2 | 9/2014 | Stearns et al. |
| 8,849,382 B2 | 9/2014 | Cox et al. |
| 8,870,872 B2 | 10/2014 | Miller |
| 8,894,654 B2 | 11/2014 | Anderson |

(56) References Cited

U.S. PATENT DOCUMENTS

| | | |
|---|---|---|
| 8,936,575 B2 | 1/2015 | Moulton |
| 8,944,069 B2 | 2/2015 | Miller et al. |
| 8,974,410 B2 | 3/2015 | Miller et al. |
| 8,998,848 B2 | 4/2015 | Miller et al. |
| 9,072,543 B2 | 7/2015 | Miller et al. |
| 9,078,637 B2 | 7/2015 | Miller |
| 9,149,625 B2 | 10/2015 | Woehr et al. |
| 9,173,679 B2 | 11/2015 | Tzachar et al. |
| 9,226,756 B2 | 1/2016 | Teisen et al. |
| 9,278,195 B2 | 3/2016 | Erskine |
| 9,295,487 B2 | 3/2016 | Miller et al. |
| 9,302,077 B2 | 4/2016 | Domonkos et al. |
| 9,314,232 B2 | 4/2016 | Stark |
| 9,314,270 B2 | 4/2016 | Miller |
| 9,358,348 B2 | 6/2016 | Weilbacher et al. |
| 9,393,031 B2 | 7/2016 | Miller |
| 9,414,815 B2 | 8/2016 | Miller et al. |
| 9,415,192 B2 | 8/2016 | Kuracina et al. |
| 9,421,345 B2 | 8/2016 | Woehr et al. |
| 9,427,555 B2 | 8/2016 | Baid |
| 9,433,400 B2 | 9/2016 | Miller |
| 9,439,667 B2 | 9/2016 | Miller |
| 9,439,702 B2 | 9/2016 | Arthur et al. |
| 9,445,743 B2 | 9/2016 | Kassab |
| 9,451,968 B2 | 9/2016 | Miller et al. |
| 9,451,983 B2 | 9/2016 | Windolf |
| 9,456,766 B2 | 10/2016 | Cox et al. |
| 9,480,483 B2 | 11/2016 | Browne et al. |
| 9,492,097 B2 | 11/2016 | Wilkes et al. |
| 9,504,477 B2 | 11/2016 | Miller et al. |
| 9,521,961 B2 | 12/2016 | Silverstein et al. |
| 9,545,243 B2 | 1/2017 | Miller et al. |
| 9,554,716 B2 | 1/2017 | Burnside et al. |
| 9,615,816 B2 | 4/2017 | Woodard |
| 9,615,838 B2 | 4/2017 | Nino et al. |
| 9,623,210 B2 | 4/2017 | Woehr |
| 9,636,031 B2 | 5/2017 | Cox |
| 9,636,484 B2 | 5/2017 | Baid |
| 9,649,048 B2 | 5/2017 | Cox et al. |
| 9,681,889 B1 | 6/2017 | Greenhalgh et al. |
| 9,687,633 B2 | 6/2017 | Teoh |
| 9,717,564 B2 | 8/2017 | Miller et al. |
| 9,730,729 B2 | 8/2017 | Kilcoin et al. |
| 9,782,546 B2 | 10/2017 | Woehr |
| 9,839,740 B2 | 12/2017 | Beamer et al. |
| 9,844,646 B2 | 12/2017 | Knutsson |
| 9,844,647 B2 | 12/2017 | Knutsson |
| 9,872,703 B2 | 1/2018 | Miller et al. |
| 9,883,853 B2 | 2/2018 | Woodard et al. |
| 9,895,512 B2 | 2/2018 | Kraft et al. |
| 9,962,211 B2 | 5/2018 | Csernatoni |
| 10,052,111 B2 | 8/2018 | Miller et al. |
| 10,092,320 B2 | 10/2018 | Morgan et al. |
| 10,092,706 B2 | 10/2018 | Denzer et al. |
| 10,159,531 B2 | 12/2018 | Misener et al. |
| 10,172,538 B2 | 1/2019 | Kassab |
| 10,413,211 B2 | 9/2019 | Kassab |
| 10,449,330 B2 | 10/2019 | Newman et al. |
| D898,908 S | 10/2020 | Denzer et al. |
| 10,893,887 B2 | 1/2021 | Blanchard |
| 10,973,532 B2 | 4/2021 | Miller et al. |
| 10,973,545 B2 | 4/2021 | Miller et al. |
| 10,980,522 B2 | 4/2021 | Muse |
| 11,298,202 B2 | 4/2022 | Miller et al. |
| 11,446,112 B2 | 9/2022 | Fink et al. |
| 11,896,264 B2 | 2/2024 | Lindekugel et al. |
| 2003/0060781 A1 | 3/2003 | Mogensen et al. |
| 2003/0225344 A1 | 12/2003 | Miller |
| 2003/0225411 A1 | 12/2003 | Miller |
| 2003/0229308 A1 | 12/2003 | Tsals et al. |
| 2004/0010236 A1 | 1/2004 | Morawski et al. |
| 2004/0059317 A1 | 3/2004 | Hermann |
| 2004/0220497 A1 | 11/2004 | Findlay et al. |
| 2004/0243135 A1 | 12/2004 | Koseki |
| 2005/0035014 A1 | 2/2005 | Cane |
| 2005/0101912 A1 | 5/2005 | Faust et al. |
| 2005/0113866 A1 | 5/2005 | Heinz et al. |
| 2005/0131345 A1 | 6/2005 | Miller |
| 2005/0165403 A1 | 7/2005 | Miller |
| 2006/0015066 A1 | 1/2006 | Turieo et al. |
| 2006/0020191 A1 | 1/2006 | Brister et al. |
| 2006/0025723 A1 | 2/2006 | Ballarini |
| 2006/0058826 A1 | 3/2006 | Evans et al. |
| 2007/0049945 A1 | 3/2007 | Miller |
| 2007/0096690 A1 | 5/2007 | Casalena et al. |
| 2007/0151116 A1 | 7/2007 | Malandain |
| 2007/0191772 A1 | 8/2007 | Wojcik |
| 2007/0270775 A1 | 11/2007 | Miller et al. |
| 2007/0276352 A1 | 11/2007 | Crocker et al. |
| 2007/0282344 A1 | 12/2007 | Yedlicka et al. |
| 2008/0015467 A1 | 1/2008 | Miller |
| 2008/0154304 A1 | 6/2008 | Crawford et al. |
| 2008/0208136 A1 | 8/2008 | Findlay et al. |
| 2008/0215056 A1 | 9/2008 | Miller et al. |
| 2008/0221580 A1 | 9/2008 | Miller et al. |
| 2008/0257359 A1 | 10/2008 | Rumsey |
| 2009/0048575 A1 | 2/2009 | Waters |
| 2009/0054808 A1 | 2/2009 | Miller |
| 2009/0093830 A1 | 4/2009 | Miller |
| 2009/0194446 A1 | 8/2009 | Miller et al. |
| 2009/0204024 A1 | 8/2009 | Miller |
| 2009/0306697 A1 | 12/2009 | Fischvogt |
| 2010/0004606 A1 | 1/2010 | Hansen et al. |
| 2010/0174243 A1 | 7/2010 | McKay |
| 2010/0204649 A1 | 8/2010 | Miller et al. |
| 2010/0286607 A1 | 11/2010 | Saltzstein |
| 2010/0298830 A1 | 11/2010 | Browne et al. |
| 2010/0298831 A1 | 11/2010 | Browne et al. |
| 2010/0312246 A1 | 12/2010 | Browne et al. |
| 2011/0004163 A1 | 1/2011 | Vaidya |
| 2011/0028976 A1 | 2/2011 | Miller |
| 2011/0202065 A1 | 8/2011 | Takizawa et al. |
| 2012/0116390 A1 | 5/2012 | Madan |
| 2012/0116394 A1 | 5/2012 | Timm et al. |
| 2012/0202180 A1 | 8/2012 | Stock et al. |
| 2012/0203154 A1 | 8/2012 | Tzachar |
| 2012/0274280 A1 | 11/2012 | Yip et al. |
| 2013/0030439 A1 | 1/2013 | Browne et al. |
| 2013/0041345 A1 | 2/2013 | Kilcoin et al. |
| 2013/0072938 A1 | 3/2013 | Browne et al. |
| 2013/0102924 A1 | 4/2013 | Findlay et al. |
| 2013/0158484 A1 | 6/2013 | Browne et al. |
| 2013/0178807 A1 | 7/2013 | Baid |
| 2014/0031674 A1 | 1/2014 | Newman et al. |
| 2014/0031794 A1 | 1/2014 | Windolf |
| 2014/0039400 A1 | 2/2014 | Browne et al. |
| 2014/0081281 A1 | 3/2014 | Felder |
| 2014/0142577 A1 | 5/2014 | Miller |
| 2014/0171873 A1 | 6/2014 | Mark |
| 2014/0188133 A1 | 7/2014 | Misener |
| 2014/0221970 A1 | 8/2014 | Eaton et al. |
| 2014/0262408 A1 | 9/2014 | Woodard |
| 2014/0262880 A1 | 9/2014 | Yoon |
| 2014/0276205 A1 | 9/2014 | Miller et al. |
| 2014/0276206 A1 | 9/2014 | Woodward et al. |
| 2014/0276471 A1 | 9/2014 | Emery et al. |
| 2014/0276833 A1 | 9/2014 | Larsen et al. |
| 2014/0276839 A1 | 9/2014 | Forman et al. |
| 2014/0343454 A1 | 11/2014 | Miller et al. |
| 2014/0343497 A1 | 11/2014 | Baid |
| 2015/0011941 A1 | 1/2015 | Saeki |
| 2015/0045732 A1 | 2/2015 | Murphy et al. |
| 2015/0080762 A1 | 3/2015 | Kassab et al. |
| 2015/0126931 A1 | 5/2015 | Holm et al. |
| 2015/0196737 A1 | 7/2015 | Baid |
| 2015/0223786 A1 | 8/2015 | Morgan et al. |
| 2015/0230823 A1 | 8/2015 | Morgan et al. |
| 2015/0238733 A1 | 8/2015 | Bin Abdulla |
| 2015/0342615 A1 | 12/2015 | Keinan et al. |
| 2015/0342756 A1 | 12/2015 | Bays et al. |
| 2015/0351797 A1 | 12/2015 | Miller et al. |
| 2015/0366569 A1 | 12/2015 | Miller |
| 2015/0367487 A1 | 12/2015 | Nino et al. |
| 2016/0009812 A1 | 1/2016 | Satelli et al. |

(56) References Cited

U.S. PATENT DOCUMENTS

| | | |
|---|---|---|
| 2016/0022282 A1 | 1/2016 | Miller et al. |
| 2016/0022284 A1 | 1/2016 | Lele et al. |
| 2016/0039916 A1 | 2/2016 | Jiang et al. |
| 2016/0058432 A1 | 3/2016 | Miller |
| 2016/0066954 A1 | 3/2016 | Miller et al. |
| 2016/0136410 A1 | 5/2016 | Aklog et al. |
| 2016/0183974 A1 | 6/2016 | Miller |
| 2016/0184509 A1 | 6/2016 | Miller et al. |
| 2016/0235949 A1 | 8/2016 | Baid |
| 2016/0305497 A1 | 10/2016 | Victor et al. |
| 2016/0354539 A1 | 12/2016 | Tan et al. |
| 2016/0361519 A1 | 12/2016 | Teoh et al. |
| 2017/0020533 A1 | 1/2017 | Browne et al. |
| 2017/0020560 A1 | 1/2017 | Van Citters et al. |
| 2017/0021138 A1 | 1/2017 | Sokolski |
| 2017/0043135 A1 | 2/2017 | Knutsson |
| 2017/0105763 A1 | 4/2017 | Karve et al. |
| 2017/0136217 A1 | 5/2017 | Riesenberger et al. |
| 2017/0151419 A1 | 6/2017 | Sonksen |
| 2017/0156740 A9 | 6/2017 | Stark |
| 2017/0156751 A1 | 6/2017 | Csernatoni |
| 2017/0209129 A1 | 7/2017 | Fagundes et al. |
| 2017/0231644 A1 | 8/2017 | Anderson |
| 2017/0303962 A1 | 10/2017 | Browne et al. |
| 2017/0303963 A1 | 10/2017 | Kilcoin et al. |
| 2018/0049772 A1 | 2/2018 | Brockman et al. |
| 2018/0092662 A1 | 4/2018 | Rioux et al. |
| 2018/0116551 A1 | 5/2018 | Newman et al. |
| 2018/0116642 A1 | 5/2018 | Woodard et al. |
| 2018/0116693 A1 | 5/2018 | Blanchard et al. |
| 2018/0117262 A1 | 5/2018 | Islam |
| 2018/0125465 A1 | 5/2018 | Muse et al. |
| 2018/0153474 A1 | 6/2018 | Aeschlimann et al. |
| 2018/0154112 A1 | 6/2018 | Chan et al. |
| 2018/0221003 A1 | 8/2018 | Hibner et al. |
| 2018/0228509 A1 | 8/2018 | Fojtik |
| 2018/0242982 A1 | 8/2018 | Laughlin et al. |
| 2019/0059986 A1 | 2/2019 | Shelton, IV et al. |
| 2019/0069812 A1 | 3/2019 | Isaacson et al. |
| 2019/0083753 A1 | 3/2019 | Chu |
| 2019/0150954 A1 | 5/2019 | Xie |
| 2019/0175220 A1 | 6/2019 | Coppedge et al. |
| 2019/0282244 A1 | 9/2019 | Muse |
| 2020/0054347 A1 | 2/2020 | Coppedge et al. |
| 2020/0054410 A1 | 2/2020 | Pfotenhauer et al. |
| 2020/0113584 A1 | 4/2020 | McGinley et al. |
| 2020/0129186 A1 | 4/2020 | Miller et al. |
| 2020/0197121 A1 | 6/2020 | Morey et al. |
| 2020/0297382 A1 | 9/2020 | Coppedge et al. |
| 2020/0297452 A1 | 9/2020 | Coppedge et al. |
| 2020/0337782 A1 | 10/2020 | Glassman et al. |
| 2021/0015529 A1* | 1/2021 | Fenton, Jr. ......... A61B 17/8847 |
| 2021/0093357 A1 | 4/2021 | Pett et al. |
| 2021/0093358 A1 | 4/2021 | Lindekugel et al. |
| 2021/0113251 A1 | 4/2021 | Vogt et al. |
| 2021/0282812 A1 | 9/2021 | Tierney et al. |
| 2021/0322055 A1 | 10/2021 | Lindekugel et al. |
| 2021/0375445 A1 | 12/2021 | Lindekugel et al. |
| 2021/0393337 A1 | 12/2021 | Zucker |
| 2022/0240976 A1 | 8/2022 | Pett et al. |
| 2022/0249104 A1 | 8/2022 | Pett et al. |
| 2022/0273338 A1 | 9/2022 | Eisenthal et al. |
| 2023/0106545 A1 | 4/2023 | Pett et al. |
| 2023/0285049 A1 | 9/2023 | Howell |
| 2023/0414251 A1 | 12/2023 | Pett et al. |
| 2024/0058036 A1 | 2/2024 | Lindekugel et al. |
| 2024/0206887 A1 | 6/2024 | Pett et al. |
| 2024/0261554 A1 | 8/2024 | Akerele-Ale et al. |
| 2024/0277375 A1 | 8/2024 | Lindekugel et al. |

FOREIGN PATENT DOCUMENTS

| | | |
|---|---|---|
| EP | 0923961 A1 | 6/1999 |
| EP | 3687024 A1 | 7/2020 |
| ES | 2390297 A1 | 11/2012 |
| FR | 2581548 A1 | 11/1986 |
| JP | 2018509969 A | 4/2018 |
| KR | 20090006621 A | 1/2009 |
| NO | 2007018809 A2 | 2/2007 |
| WO | 1997024151 A1 | 7/1997 |
| WO | 1998052638 A3 | 2/1999 |
| WO | 2005/046769 A2 | 5/2005 |
| WO | 05041790 A2 | 5/2005 |
| WO | 2005053506 A2 | 6/2005 |
| WO | 2005072625 A2 | 8/2005 |
| WO | 2008002961 A2 | 1/2008 |
| WO | 2008016757 A2 | 2/2008 |
| WO | 2008033871 A2 | 3/2008 |
| WO | 2008033872 A2 | 3/2008 |
| WO | 2008033873 A2 | 3/2008 |
| WO | 2008033874 A2 | 3/2008 |
| WO | 2008054894 A2 | 5/2008 |
| WO | 2008086258 A1 | 7/2008 |
| WO | 2008124206 A2 | 10/2008 |
| WO | 2008124463 A2 | 10/2008 |
| WO | 2008130893 A1 | 10/2008 |
| WO | 2008134355 A2 | 11/2008 |
| WO | 2008144379 A2 | 11/2008 |
| WO | 2009070896 A1 | 6/2009 |
| WO | 2010043043 A2 | 4/2010 |
| WO | 2011070593 A1 | 6/2011 |
| WO | 2011097311 A2 | 8/2011 |
| WO | 2011139294 A1 | 11/2011 |
| WO | 2013003885 A2 | 1/2013 |
| WO | 2013009901 A2 | 1/2013 |
| WO | 2013173360 A1 | 11/2013 |
| WO | 2014075165 A1 | 5/2014 |
| WO | 2014142948 A1 | 9/2014 |
| WO | 2014144239 A1 | 9/2014 |
| WO | 2014144262 A1 | 9/2014 |
| WO | 2014144489 A2 | 9/2014 |
| WO | 2014144757 A1 | 9/2014 |
| WO | 2014144797 A1 | 9/2014 |
| WO | 2015061370 A1 | 4/2015 |
| WO | 2015/177612 A1 | 11/2015 |
| WO | 2016033016 A1 | 3/2016 |
| WO | 16053834 A1 | 4/2016 |
| WO | 2016/085973 A1 | 6/2016 |
| WO | 2016163939 A1 | 10/2016 |
| WO | 18006045 A1 | 1/2018 |
| WO | 2018025094 A1 | 2/2018 |
| WO | 2018058036 A1 | 3/2018 |
| WO | 2018075694 A1 | 4/2018 |
| WO | 18098086 A1 | 5/2018 |
| WO | 2018165334 A1 | 9/2018 |
| WO | 2018165339 A1 | 9/2018 |
| WO | 2019051343 A1 | 3/2019 |
| WO | 2019/164990 A1 | 8/2019 |
| WO | 2021/011795 A1 | 1/2021 |
| WO | 2021/016122 A1 | 1/2021 |
| WO | 2021/062385 A1 | 4/2021 |
| WO | 2021062038 A1 | 4/2021 |
| WO | 2021062394 A1 | 4/2021 |
| WO | 2022/165232 A1 | 8/2022 |
| WO | 2022/170269 A1 | 8/2022 |
| WO | 2023177634 A1 | 9/2023 |
| WO | 2024163884 A1 | 8/2024 |

OTHER PUBLICATIONS

U.S. Appl. No. 17/335,870, filed Jun. 1, 2021 Final Office Action dated Mar. 26, 2024.
U.S. Appl. No. 17/405,692, filed Aug. 18, 2021 Restriction Requirement dated May 10, 2024.
U.S. Appl. No. 18/385,056, filed Oct. 30, 2023 Non-Final Office Action dated May 9, 2024.
U.S. Appl. No. 17/031,650, filed Sep. 24, 2020 Non-Final Office Action dated Jan. 19, 2022.
PCT/US2021/ 046573 filed Aug. 18, 2021 International Search Report and Written Opinion dated Nov. 30, 2021.
PCT/US2021/ 047378 filed Aug. 24, 2021 International Search Report and Written Opinion dated Nov. 17, 2021.

(56) References Cited

OTHER PUBLICATIONS

PCT/US2021/ 048542 filed Aug. 31, 2021 International Search Report and Written Opinion dated Dec. 9, 2021.
PCT/US2021/ 049475 filed Sep. 8, 2021 International Search Report and Written Opinion dated Dec. 9, 2021.
EP 19757667.1 filed Sep. 18, 2020 Extended European Search Report dated Oct. 22, 2021.
EP 20867024.0 filed Apr. 21, 2022 Extended European Search Report dated Aug. 8, 2023.
EP 20868351.6 filed Apr. 21, 2022 Extended European Search Report dated Aug. 10, 2023.
EP 23166984.7 filed Apr. 6, 2023 Extended European Search Report dated Jul. 5, 2023.
PCT/US2023/015127 filed Mar. 13, 2023 International Search Report and Written Opinion dated Jun. 26, 2023.
U.S. Appl. No. 17/035,272, filed Sep. 28, 2020 Notice of Allowance dated Jul. 7, 2023.
U.S. Appl. No. 17/235,134, filed Apr. 20, 2021 Non-Final Office Action dated Jun. 27, 2023.
U.S. Appl. No. 17/335,870, filed Jun. 1, 2021 Restriction Requirement dated Jul. 25, 2023.
U.S. Appl. No. 17/667,291, filed Feb. 8, 2022 Non-Final Office Action dated Aug. 31, 2023.
U.S. Appl. No. 17/337,100, filed Jun. 2, 2021 Notice of Allowance dated Jan. 24, 2024.
U.S. Appl. No. 17/469,613, filed Sep. 8, 2021 Non-Final Office Action dated Jan. 19, 2024.
Ekchian Gregory James et al: "Quantitative Methods for In Vitro and In Vivo Characterization of Cell and Tissue Metabolism", Jun. 11, 2018, XP055839281, retrieved from the internet on Sep. 8, 2021 : URL: https://dspace.mit.edu/bitstream/handle/1721.1/117890/1051211749-MIT.pdf?sequence=1&isAllowed=y.
PCT/US2019/ 018828 filed Feb. 20, 2019 International Preliminary Report on Patentability dated Aug. 27, 2020.
PCT/US2019/ 018828 filed Feb. 20, 2019 International Search Report and Written Opinion dated Jun. 13, 2019.
PCT/US2020/ 053119 filed Sep. 28, 2020 International Search Report and Written Opinion dated Jan. 5, 2021.
PCT/US2020/052558 filed Sep. 24, 2020 International Search Report and Written Opinion dated Feb. 11, 2021.
PCT/US2020/053135 filed Sep. 28, 2020 International Search Report and Written Opinion dated Dec. 18, 2020.
PCT/US2021/ 035232 filed Jun. 1, 2021 International Search Report and Written Opinion dated Oct. 19, 2021.
PCT/US2021/028114 filed Apr. 20, 2021 International Search Report and Written Opinion dated Jul. 12, 2021.
PCT/US2021/035475 filed Jun. 2, 2021 International Search Report and Written Opinion dated Sep. 17, 2021.
PCT/US2022/014391 filed Jan. 28, 2022 International Search Report and Written Opinion dated Apr. 14, 2022.
PCT/US2022/015686 filed Feb. 8, 2022 International Search Report and Written Opinion dated May 25, 2022.
U.S. Appl. No. 17/031,650, filed Sep. 24, 2020 Final Office Action dated Jul. 20, 2022.
U.S. Appl. No. 17/035,336, filed Sep. 28, 2020 Restriction Requirement dated Jul. 26, 2022.
U.S. Appl. No. 17/235,134, filed Apr. 20, 2021 Notice of Allowance dated Sep. 20, 2023.
U.S. Appl. No. 17/335,870, filed Jun. 1, 2021 Non-Final Office Action dated Nov. 15, 2023.
U.S. Appl. No. 17/337,100, filed Jun. 2, 2021 Final Office Action dated Nov. 21, 2023.
U.S. Appl. No. 17/469,613, filed Sep. 8, 2021 Restriction Requirement dated Oct. 23, 2023.
U.S. Appl. No. 17/863,898, filed Jul. 13, 2022 Final Office Action dated Nov. 22, 2023.
U.S. Appl. No. 17/031,650, filed Sep. 24, 2020 Notice of Allowance dated Oct. 12, 2022.
U.S. Appl. No. 17/035,272, filed Sep. 28, 2020 Non-Final Office Action dated Mar. 9, 2023.
U.S. Appl. No. 17/035,272, filed Sep. 28, 2020 Restriction Requirement dated Dec. 9, 2022.
U.S. Appl. No. 17/035,336, filed Sep. 28, 2020 Notice of Allowance dated Jan. 11, 2023.
U.S. Appl. No. 17/235,134, filed Apr. 20, 2021 Restriction Requirement dated Mar. 7, 2023.
U.S. Appl. No. 17/337,100, filed Jun. 2, 2021 Non-Final Office Action dated Jun. 2, 2023.
U.S. Appl. No. 17/667,291, filed Feb. 8, 2022 Restriction Requirement dated May 31, 2023.
U.S. Appl. No. 17/405,692, filed Aug. 18, 2021 Non-Final Office Action dated Sep. 6, 2024.
U.S. Appl. No. 17/463,324, filed Aug. 31, 2021 Non-Final Office Action dated Oct. 30, 2024.
U.S. Appl. No. 17/463,324, filed Aug. 31, 2021 Restriction Requirement dated Aug. 8, 2024.
U.S. Appl. No. 17/587,900, filed Jan. 28, 2022 Non-Final Office Action dated Nov. 14, 2024.
U.S. Appl. No. 18/075,269, filed Dec. 5, 2022 Non-Final Office Action dated Jun. 24, 2024.
U.S. Appl. No. 18/075,269, filed Dec. 5, 2022 Notice of Allowance dated Sep. 11, 2024.
U.S. Appl. No. 18/244,730, filed Sep. 11, 2023 Final Office Action dated Aug. 8, 2024.
U.S. Appl. No. 18/244,730, filed Sep. 11, 2023 Non-Final Office Action dated May 3, 2024.
U.S. Appl. No. 18/244,730, filed Sep. 11, 2023 Notice of Allowance dated Oct. 24, 2024.
U.S. Appl. No. 18/385,056, filed Oct. 30, 2023 Notice of Allowance dated Aug. 29, 2024.
U.S. Appl. No. 17/405,692, filed Aug. 18, 2021 Final Office Action dated Dec. 4, 2024.
U.S. Appl. No. 17/469,613, filed Sep. 8, 2021 Final Office Action dated Dec. 6, 2024.

\* cited by examiner

ANGLED INTRAOSSEOUS ACCESS SYSTEM

PRIORITY

This application claims the benefit of priority to U.S. Provisional Application No. 63/069,988, filed Aug. 25, 2020, which is incorporated by reference in its entirety into this application.

BACKGROUND

Intraosseous (IO) access devices can provide vascular access by penetrating surface tissues and underlying hard bone cortex layers to place an access needle and provide access to a medullary cavity of a bone. Fluids and medications can flow through the needle lumen and into the medullary cavity to infuse into the vascular system. IO access events are typically performed in emergent situations where vascular access is rapidly required and/or direct venous access is not possible.

Patients who require IO access report experiencing increased pain during infusion rather than during penetration of the skin surface tissues or bone cortex. The cause of pain may be due to increased pressure in the medullary cavity due to the infused fluids and/or medication. Angling the needle during insertion may direct medication towards larger volumes of the medullary cavity, e.g. the tibial tuberosity, reducing the pressure within the medullary cavity, and in turn reducing discomfort. Further, angling the needle during penetration can mitigate "backwalling," where the access needle traverses the medullary cavity and penetrates the far wall of bone cortex. Disclosed herein are angled intraosseous access systems including an angled guide plate and an angled guide block, and associated methods thereof that address the foregoing.

SUMMARY

Disclosed herein is an angled intraosseous access system including, a needle assembly including a needle defining a needle axis and configured to access a medullary cavity of a bone, a driver rotatably coupled to the needle assembly and configured to advance the needle through a bone cortex to access the medullary cavity, and one or both of a guide plate and a guide block configured to engage a skin surface and align the needle axis at a predetermined angle relative to a longitudinal axis of the medullary cavity.

In some embodiments, the predetermined angle is between 1°-90° relative to the longitudinal axis of the medullary cavity. In some embodiments, one of the guide plate or the guide block includes a concave or convex skin engaging surface configured to engage the skin surface. In some embodiments, the guide plate is coupled to the guide block. In some embodiments, one of the guide plate or the guide block includes a guide recess configured to engage a fiduciary body part and align the needle with a target location. In some embodiments, the guide recess is disposed on a first portion that is slidably engaged with a second portion of one of the guide plate or the guide block which is coupled to the needle.

In some embodiments, the guide block includes a first series of notches and a second series of notches each configured to receive a portion of the driver, the first series of notches configured to align the needle axis with a first predetermined angle, the second series of notches configured to align the needle axis with a second predetermined angle different from the first predetermined angle. In some embodiments, the guide plate defines a channel configured to receive the needle therethrough and maintain the needle at the predetermined angle. In some embodiments, one of the guide plate or the guide block is releasably engaged with the driver body.

In some embodiments, one or both of the guide plate and the guide block includes an adhesive disposed on a surface thereof and configured to adhere to one or both of the driver and the skin surface. In some embodiments, a portion of the guide plate is configured to abut against a portion of the needle assembly to prevent a distal tip of the needle from backwalling a far wall of the medullary cavity.

Also disclosed is a method of accessing a medullary cavity including, engaging a skin engaging surface of a guide plate with a skin surface, aligning a needle of an intraosseous access system with a channel of the guide plate, the channel extending at a predetermined angle relative to the skin engaging surface, and advancing the needle through the channel to access the medullary cavity at the predetermined angle.

In some embodiments, the predetermined angle is between 1°-90° relative to a longitudinal axis of the medullary cavity. In some embodiments, the skin engaging surface includes a concave or a convex portion configured to engage the skin surface. In some embodiments, the method further includes coupling the guide plate with a guide block configured to engage the skin surface and a driver of the intraosseous access system and maintain an axis of the driver at the predetermined angle. In some embodiments, the method further includes engaging a guide recess, disposed on the skin engaging surface, with a fiduciary body part to align the needle with a target location.

In some embodiments, the method further includes sliding a first portion of the guide plate including the guide recess disposed thereon, relative to a second portion of the guide plate including the channel, to align the needle with a target location. In some embodiments, the method further includes adhering a portion of the guide plate to one of the driver or the skin surface. In some embodiments, the method further includes abutting a portion of a needle hub, coupled to the needle against a surface of the guide plate to prevent a distal tip of the needle from backwalling a far wall of the medullary cavity.

Also disclosed is a method of accessing a medullary cavity including, engaging a portion of a driver of an intraosseous access system with a surface of the guide block, engaging a skin engaging surface of the guide block with a skin surface, aligning an axis of a needle of the intraosseous access system with a predetermined angle, and advancing the needle along the needle axis to access the medullary cavity at the predetermined angle.

In some embodiments, the predetermined angle is between 1°-90° relative to a longitudinal axis of the medullary cavity. In some embodiments, the method further includes engaging a guide recess disposed on the skin engaging surface with a fiduciary body part to align the needle with a target location. In some embodiments, the method further includes sliding a first portion of the guide block including the guide recess disposed thereon, relative to a second portion of the guide block to align the needle with a target location. In some embodiments, the method further includes engaging the portion of the driver with one of a first series of notches or a second series of notches to align the axis of the needle axis with one of a first predetermined angle or a second predetermined angle, different from the first predetermined angle.

These and other features of the concepts provided herein will become more apparent to those of skill in the art in view of the accompanying drawings and following description, which describe particular embodiments of such concepts in greater detail.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a needle disclosed herein includes a portion of the needle intended to be near a clinician when the needle is used on a patient. Likewise, a "proximal length" of, for example, the needle includes a length of the needle intended to be near the clinician when the needle is used on the patient. A "proximal end" of, for example, the needle includes an end of the needle intended to be near the clinician when the needle is used on the patient. The proximal portion, the proximal-end portion, or the proximal length of the needle can include the proximal end of the needle; however, the proximal portion, the proximal-end portion, or the proximal length of the needle need not include the proximal end of the needle. That is, unless context suggests otherwise, the proximal portion, the proximal-end portion, or the proximal length of the needle is not a terminal portion or terminal length of the needle.

With respect to "distal," a "distal portion" or a "distal-end portion" of, for example, a needle disclosed herein includes a portion of the needle intended to be near or in a patient when the needle is used on the patient. Likewise, a "distal length" of, for example, the needle includes a length of the needle intended to be near or in the patient when the needle is used on the patient. A "distal end" of, for example, the needle includes an end of the needle intended to be near or in the patient when the needle is used on the patient. The distal portion, the distal-end portion, or the distal length of the needle can include the distal end of the needle; however, the distal portion, the distal-end portion, or the distal length of the needle need not include the distal end of the needle. That is, unless context suggests otherwise, the distal portion, the distal-end portion, or the distal length of the needle is not a terminal portion or terminal length of the needle.

Unless defined otherwise, all technical and scientific terms used herein have the same meaning as commonly understood by those of ordinary skill in the art.

Figure 1A:
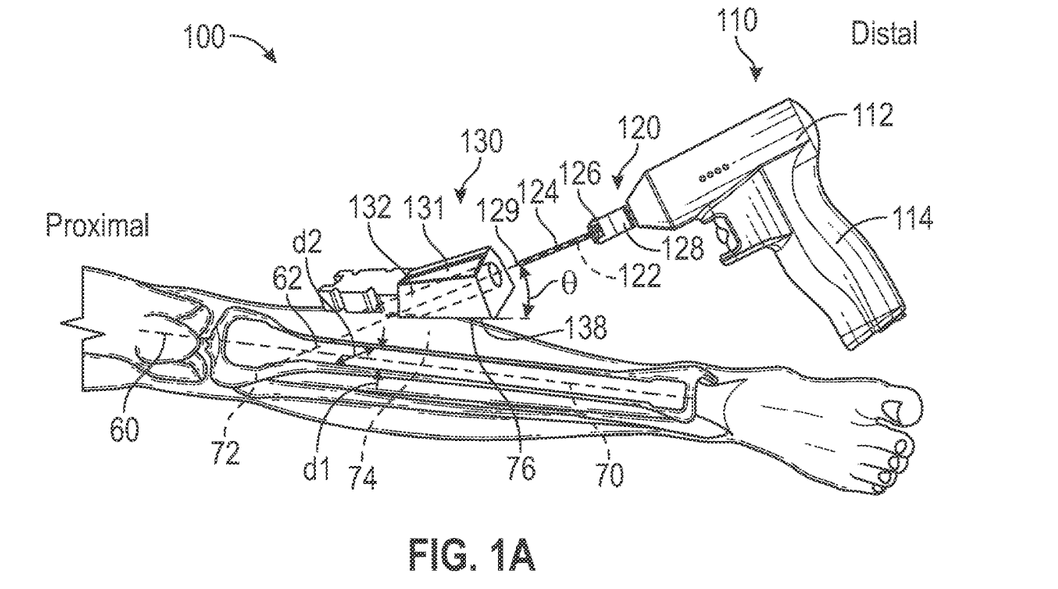
FIG. 1A illustrates a perspective view of a guide plate angled IO access system, in accordance with some embodiments.
Figure 1B:
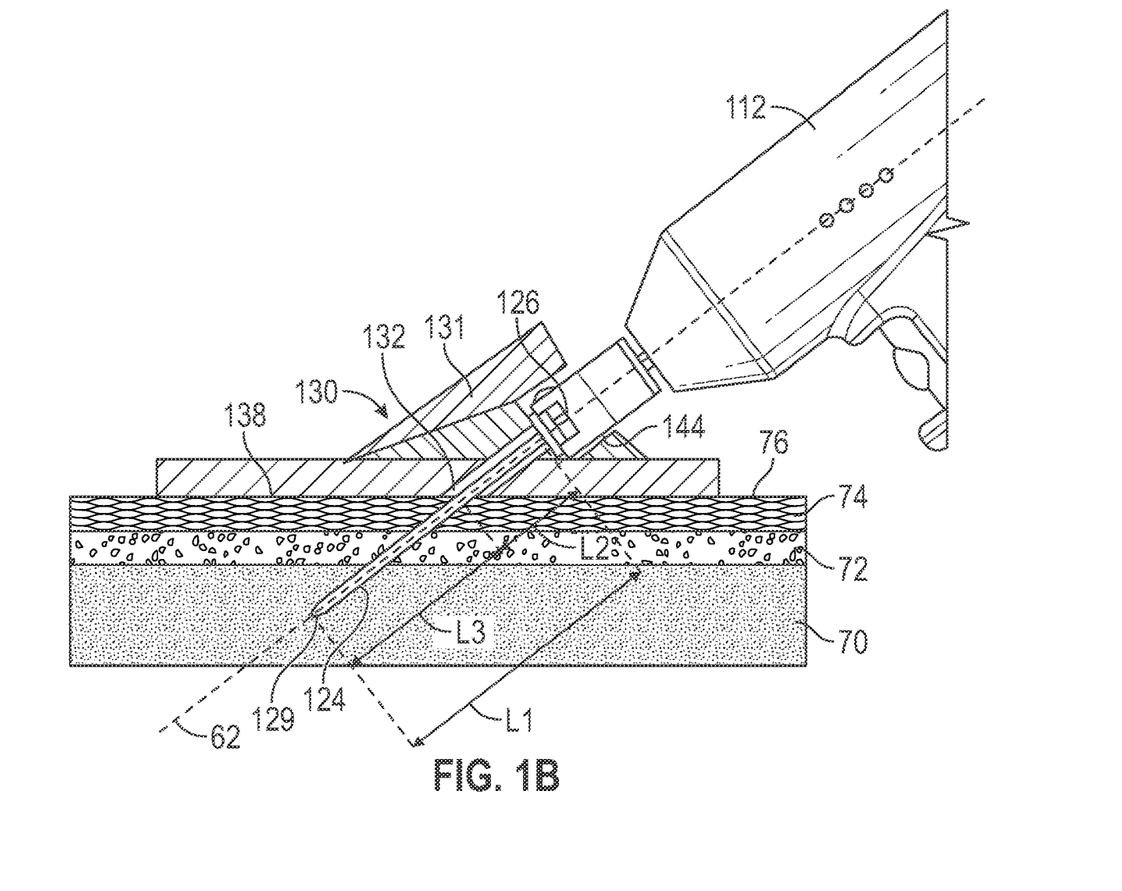
FIG. 1B illustrates close up detail of a needle engaged with an angled guide plate, in accordance with some embodiments.

FIGS. 1A-1B show embodiments of a guide plate angled intraosseous (IO) access system 100 configured to penetrate a bone cortex 72 and surface tissues 74 to access a medullary cavity 70. In an embodiment, the guide plate angled IO access system 100 generally includes an IO access system 110 and an angled guide plate ("guide plate") 130. The IO access system 110 generally includes a driver 112 having a body 114, and a needle assembly 120 rotatably coupled to the driver 112. In an embodiment, the driver 112 includes an automatic driver or a manual driver configured to rotate the needle assembly 120 and drill a needle 124 through the surface tissues 74 and bone cortex 72, access a medullary cavity 70 of a bone of a patient.

In an embodiment, the driver 112 can include a drive spring, electric motor, or similar electrical, mechanical, electro-mechanical, or kinetic mechanism configured to rotate the needle assembly 120 and drill the needle assembly into a bone of a patient. In an embodiment, the needle assembly 120 can include a needle 124 defining a lumen and supported by a needle hub 126. The needle assembly 120 can further include an obturator 122 disposed within the lumen of the needle 124 and supported by an obturator hub 128. The obturator 122 can be configured to prevent tissue and bone fragments from entering the needle lumen during a placement event and occluding a fluid flow through the needle lumen. Once the needle 124 has been placed, the driver 110 and obturator 122 can be removed. Fluids and/or medications can flow through the needle lumen and into the medullary cavity 70 to infuse into the vasculature of the patient. Further details and embodiments of IO access systems can be found, for example in the following published applications: US 2021/0093354, US 2021/0093355, US 2021/0093358, US 2021/0093356, US 2021/0093357, US 2021/0137558, WO 2018/075694, WO 2018/165334, and WO 2018/165339, each of which are incorporated by reference in its entirety herein.

In an embodiment, the guide plate 130 includes a body 131 defining a skin engaging surface 138, and a channel 132 extending at an angle (θ) relative to a longitudinal axis of the body 131. In an embodiment, the skin engaging surface 138 can be a bottom surface of the body 131. However, it will be appreciated that the skin engaging surface 138 can include one or more surfaces of the body 131. In an embodiment, the skin engaging surface 138 of the guide plate 130 can engage a skin surface 76 and align the channel 132 at an angle (θ) relative thereto. In an embodiment, the guide plate 130 align the channel 132 at an angle (θ) relative to a longitudinal axis 60 of the medullary cavity 70. In an embodiment, the angle (θ) of the channel 132 can be between 1° and 90°. In an embodiment, the angle (θ) of the channel 132 can be between 10°-75°. In an embodiment, the angle (θ) of the channel 132 can be substantially 45°, however greater or lesser angles are also contemplated.

In an embodiment, a diameter of the channel 132 can be equal to or slightly larger than a diameter of the needle 124. As such, the needle 124 can slidably engage the channel 132 and substantially align an axis 62 of the needle 124 with an axis of the channel 132. In some embodiments, the diameter of the guide plate channel 132 may be a consistent diameter along the length thereof. In some embodiments, the guide plate channel 132 or portion thereof may define a tapered shape, having a greater diameter proximate a first end relative to a second end, opposite the first end. In some embodiments, an entrance of the guide plate channel 132 may be tapered to facilitate aligning a needle 124 with the channel 132.

In an exemplary method of use, a user can engage a skin engaging surface 138 of the guide plate 130 with a skin surface 76 and align the channel 132 with a target insertion site. The user can then align the needle 124 with the channel 132 and advance a distal tip 129 of the needle 124 through the channel 132. Advancing the needle 124 through the channel 132 can align an axis 62 of the needle 124 with the axis of the channel 132. A user can then actuate the driver 112 to rotate the needle assembly 120 and "drill" the needle 124 into the patient. The needle 124 can then penetrate the surface tissues 74, hard bone cortex 72 and the medullary cavity 70 at the predetermined angle (θ) defined by the channel 132.

In an embodiment, the guide plate 130 can be coupled to the IO access system 110 and the guide plate 130 can be slidably engaged with the needle 124. As such, a user can support the skin engaging surface 138 against the skin surface 76 and the guide plate 130 can further support the IO access system 110 with the needle axis 62 aligned with the channel 132. The user can then actuate the driver 112 and urge the IO access system 110 including the needle 124 along the needle axis 62 at the predetermined angle (θ) defined by the channel 132. The needle 124 can slide through the channel 132 to penetrate the bone at the predetermined angle (θ), as described herein.

In an embodiment, the guide plate 130 can be coupled to the IO access system 110, and the needle assembly 120 can be slidably engaged relative to the IO access system 110 and guide plate 130 assembly. As such, a user can support the skin engaging surface 138 against the skin surface 76 and the guide plate 130 can further support the IO access system 110 with the needle axis 62 aligned with the channel 132. The user can then actuate the driver 112 and the IO access system 110 can urge the needle 124 along the needle axis 62 to penetrate the bone at the predetermined angle (θ), as described herein.

Advantageously, the insertion angle (θ) of the needle 124 can direct a fluid flow through the needle lumen towards the wider regions of the medullary cavity 70, for example at a head of the bone, and can reduce the pressure within the medullary cavity 70 as the fluids and/or medications are transfused. Advantageously, the guide plate 130 can be configured to align the needle 124 at an angle (θ) relative to the axis 60 of the medullary cavity 70 and can increase the penetrable depth (d) of the medullary cavity 70. As shown in FIG. 1A, for a given location within the medullary cavity 70, a perpendicular penetrable depth (d1) (i.e. when the needle is angled perpendicular to the axis 60 of the medullary cavity 70) is less than an angled penetrable depth (d2) (i.e. when the needle is angled (θ) relative to the medullary axis 60). As such, the angled penetrable depth (d2) mitigates the needle 124 from "backwalling" the far side of the medullary cavity 70. Further, in an embodiment, the guide plate 130 can be configured to align the needle 124 with the widest portion of the medullary cavity 70, e.g. at the head of the bone, as described in more detail herein.

In an embodiment, as shown in FIG. 1B, the length of the needle 124 extending between the needle hub 126 at a proximal end and a distal tip 129 can define a first length (L1). The channel 132 can define a second length (L2), less than the first length (L1), and extending axially. In an embodiment, the needle 124 can be advanced through the channel 132 until the distal tip 129 extends through the skin engaging surface 138 and a portion of the hub 126 abuts against a portion of the guide plate body 131, proximate the channel entrance 132. As such, with the skin engaging surface 138 contacting the skin surface 76, the distal tip 129 can extend through the channel 132 and penetrate the underlying tissues 74, bone cortex 72, etc. In an embodiment, the length (L2) of the channel 132 can be predetermined such that a portion of the needle 124 extends through the surface tissues 74, bone cortex 72 and into the medullary cavity 70 by a penetration length, or third length (L3). In an embodiment, the third length (L3) is the length of the needle (L1) less the length (L2) of the channel 132. Advantageously, the length (L1) of the needle 124 and the length (L2) of the channel 132 can be predetermined to ensure the penetration length (L3) of the needle 124 is less than a penetration length that would "backwall" the medullary cavity 70. This can prevent a user from over penetrating the needle 124 during an emergency placement event.

In an embodiment, as shown in FIG. 1B, the guide plate 130 can further include a needle hub slot 144 configured to receive a portion of the needle hub 144 therein. Advantageously, the needle hub slot 144 can be configured to facilitate aligning the axis 62 of the needle with axis of the channel 132. In an embodiment, the needle hub 126 can abut against a portion of the needle hub slot 144 to prevent the distal tip 129 of the needle 124 from extending beyond the predetermined penetrable length (L3), mitigating backwalling of the medullary cavity 70.

Figure 2:
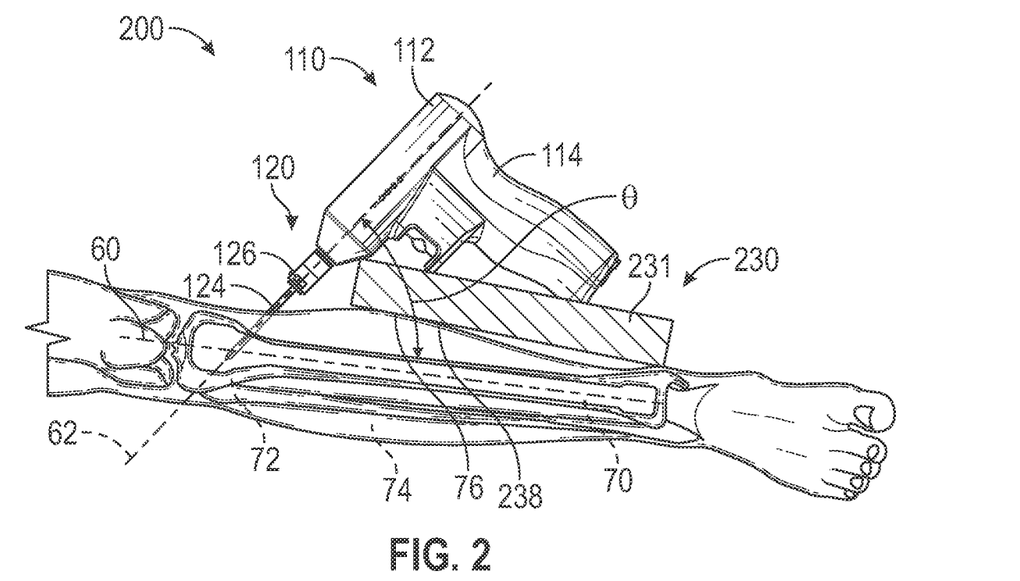
FIG. 2 illustrates a side view of a guide block angled IO access system, in accordance with some embodiments.

In an embodiment, as shown in FIG. 2, an angled IO access system 200 can include a guide block 230, configured to engage one or both of the IO access system 110 and the skin surface 76 and align the needle 124 at an angle (θ) relative to the skin surface 76 and/or an axis 60 of the medullary cavity 70. In an embodiment, the guide block 230 includes a body 231 having a skin engaging surface 238. In an embodiment, the skin engaging surface 238 can be a bottom surface of the body 231. However, it will be appreciated that the skin engaging surface 138 can include one or more surfaces of the body 231. Advantageously, the guide block 230 provides a stable surface for IO access system 110 to rest on.

In an embodiment, the guide block 230 can be integrally formed with the driver body 114. In an embodiment, the guide block 230 can be coupled to a portion of the driver body 114 using adhesive, bonding, welding, bolts, screws, or similar fasteners, or similar suitable means. In an embodiment, the guide block 230 can be releasably coupled with the driver body 114 using a clip, latch, interference fit, press-fit, or snap-fit engagement, or similar suitable mechanism.

In an embodiment, a user can grasp the driver body 114 with the guide block 230 coupled thereto, and engage the skin engaging surface 238 with the skin surface 76 of the patient. As such, an axis 62 of the needle 124 can be positioned at a predetermined angle (θ) relative to the axis 60 of the medullary cavity 70, as described herein.

In an embodiment, the IO access system 110 can be slidably engaged with the guide block 230 along the axis 62 of the needle 124. In an embodiment, the needle assembly 120 or portions thereof can be slidable relative to one or both of the driver 112 and the guide block 230, along the axis 62 of the needle 124. As such, the skin engaging surface 238 of the guide block 230 can engage the skin surface 76 and angle the axis 62 of the needle 124 relative to the axis 60 of the medullary cavity 70, as described herein. The needle 124 can then slide along the needle axis 62 through the surface tissues 74, bone cortex 72, and access the medullary cavity 70, as described herein.

Figure 3:
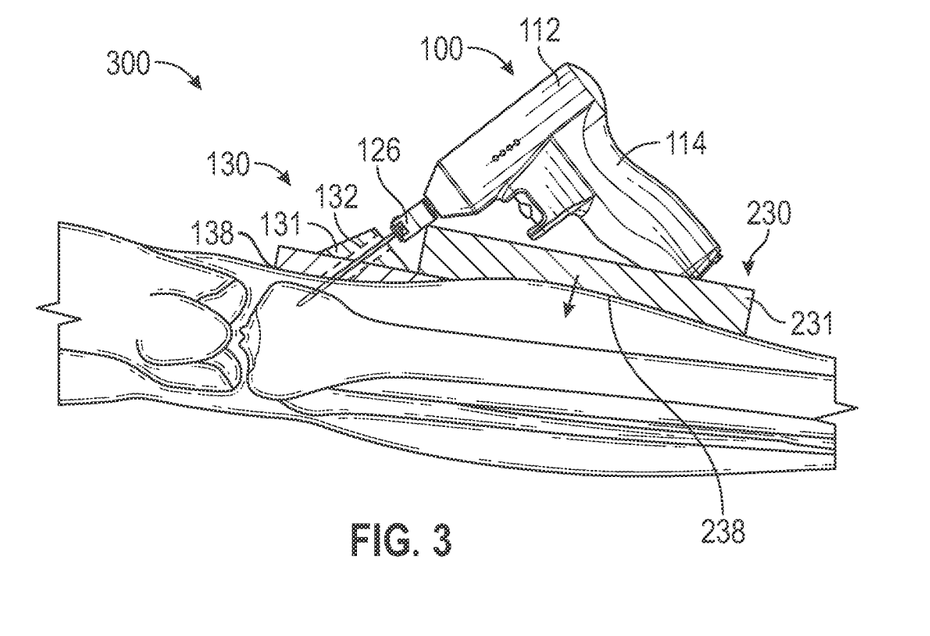
FIG. 3 illustrates a side view of a combination angled IO access system including a guide plate and a guide block, in accordance with some embodiments.

In an embodiment, as shown in FIGS. 1A-2, one of the skin engaging surface 138 of the guide plate 130, or the skin engaging surface 238 of the guide block 230 can define a substantially flat surface. As shown in FIG. 3, in an embodiment, the skin engaging surface 138 of the guide plate 130, or the skin engaging surface 238 of the guide block 230 can include a regular or irregular concave or convex surface configured to substantially match a curved shape of a skin surface 76.

In an embodiment, as shown in FIG. 3, an angled IO access system 300 can include both the guide plate 130, and the guide block 230 to support and guide the IO access system 110 at a predetermined angle (θ) relative to the skin surface 76. In some embodiments, the guide plate 130 can be coupled to the guide block 230 to provide the user with a stable surface to rest a portion of the body 114 of the driver 112 and provide a guide for accessing the medullary cavity 70 at a predetermined angle (θ), as described herein.

In an embodiment, the guide plate 130 can be integrally formed with the guide block 230. In an embodiment, the guide plate 130 can be coupled to a portion of the guide block 230 using adhesive, bonding, welding, bolts, screws, or similar fasteners, or similar suitable means. In an embodiment, the guide plate 130 can be releasably coupled with the guide block 230 using a clip, latch, interference fit engagement, press-fit engagement, snap-fit engagement, hook, tab, slot, or similar suitable mechanism, or combinations thereof. Advantageously, the guide plate 130 and the guide block 230 being coupled together can offer increased stability during a medullary access event to ensure accurate placement of the access needle 124.

In an embodiment, one or more surfaces of the guide plate body 131 or the guide block body 231 can include an adhesive or the like. For example, the adhesive surface can be disposed on a skin engaging surface 138, 238 to facilitate securing the guide plate 130 or guide block 230 to the skin surface 76. In an embodiment, the adhesive surface can be configured to secure one or both of the guide plate 130 and the guide block 230 relative to the IO access system 110. In an embodiment, one or more surfaces of the guide plate 131 or the guide block body 231 can include a material, e.g. silicone rubber, or the like, having a high frictional coefficient to facilitate securing the guide plate 130 or guide block 230 relative to the skin surface 76, or to the IO access system 110, or combinations thereof.

Figure 4:
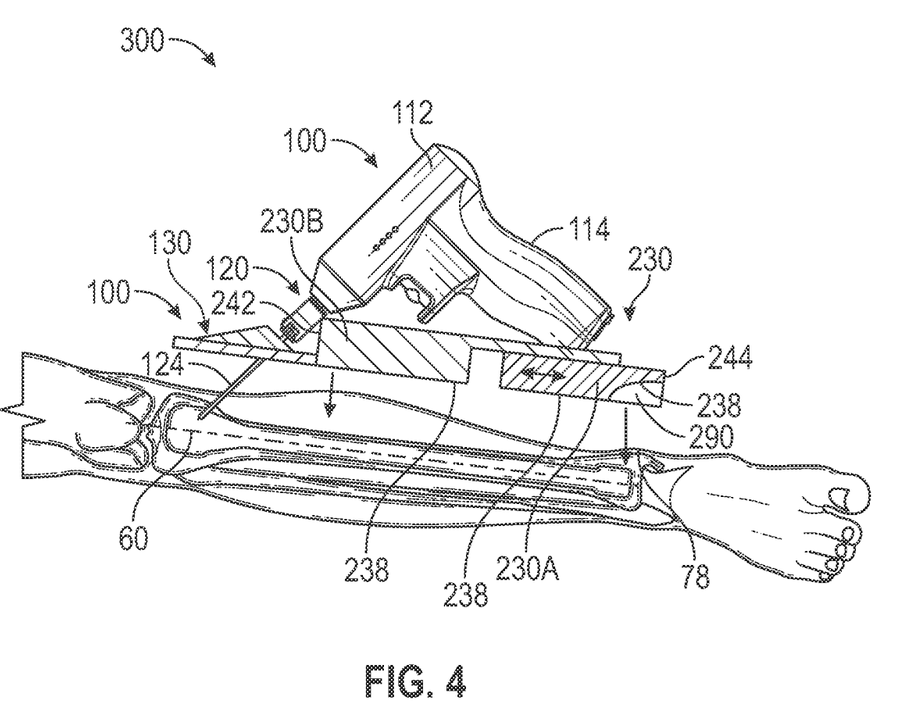
FIG. 4 illustrates a side view of a combination angled IO access system including a guide block having a slidable portion, in accordance with some embodiments.

As shown in FIG. 4, in an embodiment, one of the guide plate 130 or the guide block 230 can include a guide recess 290 configured to engage a fiduciary body part 78 and to facilitate alignment of the needle 124 with a target area of bone. For example, a skin engaging surface 238 of the guide block 230 can include a guide recess 290 configured to receive the fiduciary body part 78, e.g. ankle bone, wrist bone, or the like, and to facilitate alignment of the needle 124 with a target area of bone. The driver 112 can be coupled to the guide block 230 with a needle assembly 120 disposed proximate a first end 242. The guide recess 290 can be disposed on a skin engaging surface 238 proximate a second end 244, disposed opposite the first end 242 along an axis of the guide block 230 extending substantially parallel to the skin surface 76 or the axis 60 of the medullary cavity 70. In an embodiment, the guide recess 290 can be a regular or irregular concave shape and can be configured to engage a fiduciary body part 78, e.g. an ankle bone or the like. When the guide block 230 is aligned with the fiduciary body part 78, the needle 124 of the IO access system 110 will be aligned at an angle (θ) with a target area of bone, e.g. a tibial tuberosity, or the like.

Advantageously, the guide block 230 including the guide recess 290 can quickly and intuitively align the needle 124 with a target area of the bone, e.g. the widest portion of the medullary cavity 70, during an emergency placement event where time and availability of trained personnel may be limited. Further, the guide block 230 can angle the needle 124 relative to the axis 60 of the medullary cavity 70 to further increase a penetrable depth for the needle 124.

In an embodiment, a portion of the guide plate 130 or the guide block 230 can be slidably engaged therewith, to allow a user to adjust the position of the guide recess 290 relative to the needle 124. For example, as shown in FIG. 4, a first portion 230A of the guide block 230 that includes the guide recess 290 can be slidably engaged with a second portion 230B of the guide block 230 that supports the IO access system 110. As such, the distance between the guide recess 290 and the needle 124 of the IO access system 110 can be modified to suit different size bones of different patients. For example, taller patients may have a greater distance between the ankle body and the tibial tuberosity than shorter patients.

In an exemplary method of use, the guide plate 130 and guide block 230 assembly can engage a skin surface 76 of a patient. In an embodiment, a concave or convex skin engaging surface 138, 238 can engage a curved skin surface 76 of the patient. In an embodiment, a guide recess 290 can engage a fiduciary body part 78 to align the needle 124 with a target area. In an embodiment, the user can adjust a first portion 230A of the guide block 230 relative to a second portion 230B and engage the guide recess 290 with the fiduciary body part 78. In an embodiment, the user can align the needle 124 with the channel 132. In an embodiment, the needle 124 can be "preloaded" within the channel 132 prior to the system 300 engaging the skin surface 76. The user can then actuate the driver 112 to rotate the needle assembly 120. In an embodiment, the IO access system 100 can slide relative to one of the guide plate 130 or the guide block 230 to advance the needle 124 through the channel 132. In an embodiment, the needle assembly 120 can advance through the channel 132 relative to the driver 112. The needle can then penetrate the bone at the predetermined angle (θ) to access the medullary cavity 70, as described herein.

Figure 5A:
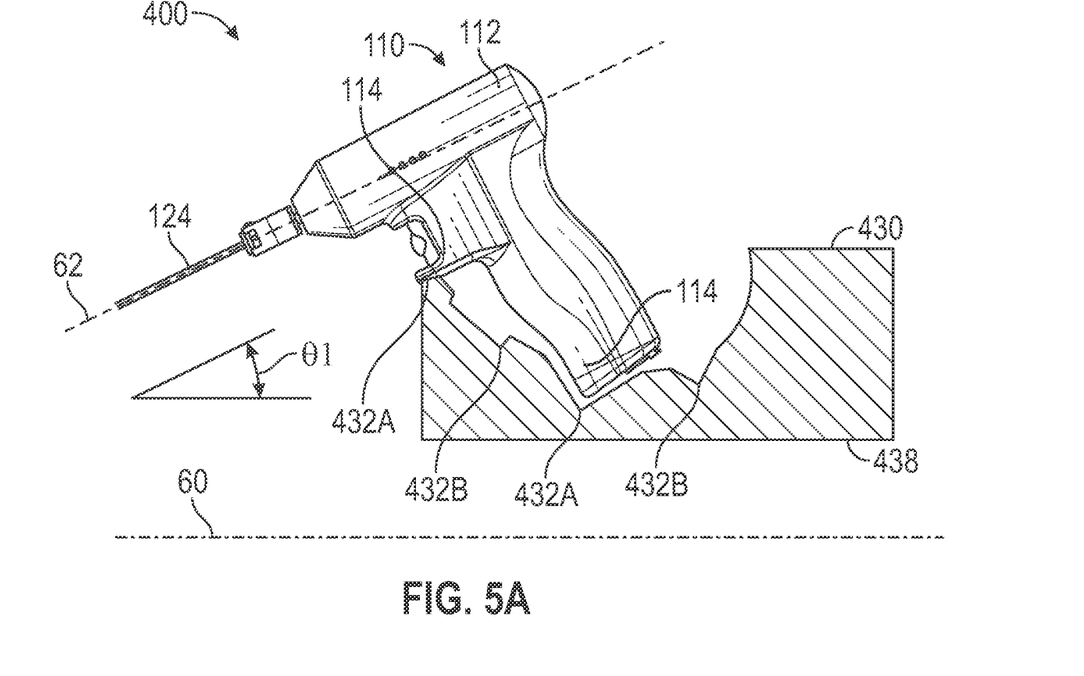
FIGS. 5A-5B illustrate side views of a guide block angled IO access system, in accordance with some embodiments.
Figure 5B:
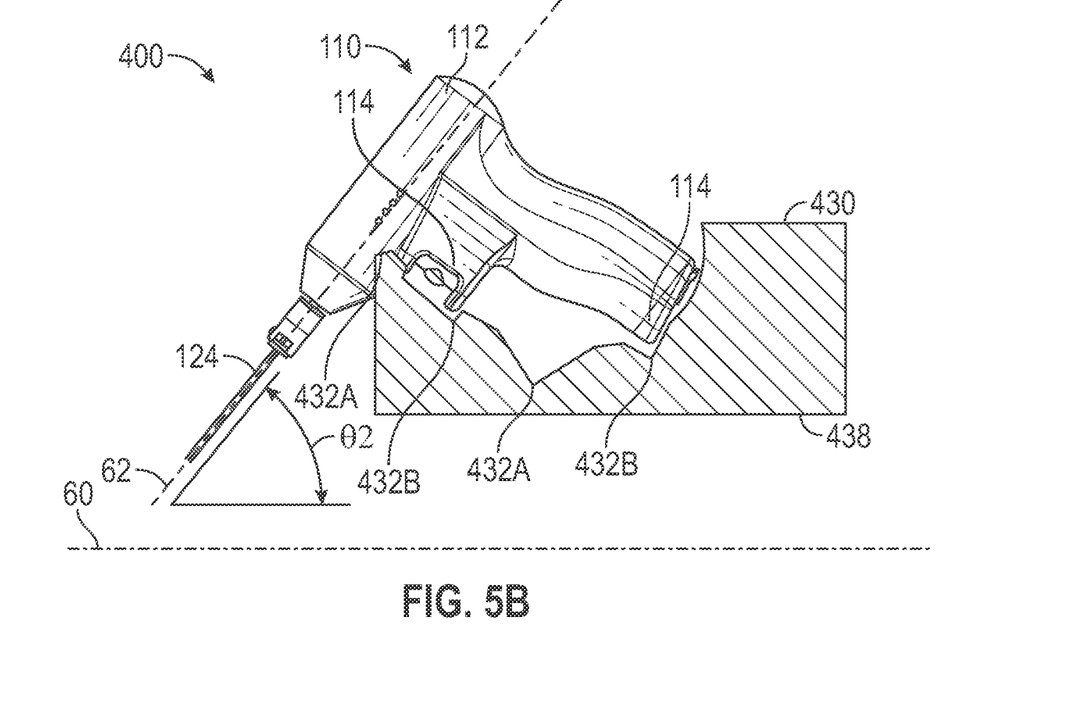

FIGS. 5A-5B show an embodiment of an adjustable angle IO access system 400 including a guide block 430 having a skin engaging surface 438 and one or more notches 432 disposed on one or more surfaces of the guide block 430. The one or more notches 432 can be configured to receive a portion of the driver body 114 and position the driver 112 at one or more predetermined angles relative to the axis 60 of the medullary cavity 70 when the skin engaging surface 438 engages a skin surface 76.

For example, as shown in FIG. 5A, a first series of notches 432A of the one or more notches 432 can receive one or more portions of the driver body 114 and position an axis 62 of the needle 124 at a first angle (θ1) relative to the skin surface 76 and/or medullary cavity axis 60. As shown in FIG. 5B, a second series of notches 432B of the one or more notches 432 can receive one or more portions of the driver body 114 and position an axis 62 of the needle 124 at a second angle (θ2) relative to the skin surface 76 and/or medullary cavity axis 60 different from the first angle (θ1). In an embodiment, one of the first angle (θ1) or the second angle (θ2) can be between 1°-90° relative to the axis 60 of the medullary cavity 70. In an embodiment, the guide block 430 can include one or more symbols, alphanumeric symbols, color codes, textures, or the like to indicate which series of notches 432 corresponds with which predetermined angles (θ1, θ2).

In an exemplary method of use, a skin engaging surface 438 of the guide block 430 can engage a skin surface 76 of the patient. The user can align a portion of the driver body 114 with one of the first series of notches 432A or the second series of notches 432B to selectively align an axis 62 of the needle 124 with one of the first angle (θ1) or the second angle (θ2). The user can then actuate the driver 112 to rotate the needle assembly 120 and advance the needle 124 into the medullary cavity 70, as described herein, at one of the first angle (θ1) or the second angle (θ2).

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An angled intraosseous access system, comprising:
   a needle assembly including a needle defining a needle axis and configured to access a medullary cavity of a bone;
   a driver rotatably coupled to the needle assembly and configured to advance the needle through a bone cortex to access the medullary cavity; and
   a guide plate and a guide block configured to engage a skin surface and align the needle axis at a predetermined angle relative to a longitudinal axis of the medullary cavity; wherein the guide block includes a first series of notches and a second series of notches each configured to receive a portion of the driver, the first series of notches configured to align the needle axis with a first predetermined angle, the second series of notches configured to align the needle axis with a second predetermined angle different from the first predetermined angle.

2. The angled intraosseous access system according to claim 1, wherein the predetermined angle is between 1°-90° relative to the longitudinal axis of the medullary cavity.

3. The angled intraosseous access system according to claim 1, wherein one of the guide plate or the guide block includes a concave or convex skin engaging surface configured to engage the skin surface.

4. The angled intraosseous access system according to claim 1, wherein the guide plate is coupled to the guide block.

5. The angled intraosseous access system according to claim 1, wherein one of the guide plate or the guide block includes a guide recess configured to engage a an anatomical landmark body part and align the needle with a target location.

6. The angled intraosseous access system according to claim 5, wherein the guide recess is disposed on a first portion that is slidably engaged with a second portion of one of the guide plate or the guide block which is coupled to the needle.

7. The angled intraosseous access system according to claim 1, wherein the guide plate defines a channel configured to receive the needle therethrough and maintain the needle at the predetermined angle.

8. The angled intraosseous access system according to claim 1, wherein one of the guide plate or the guide block is releasably engaged with a driver body.

9. The angled intraosseous access system according to claim 1, wherein one or both of the guide plate and the guide block includes an adhesive disposed on a surface thereof and configured to adhere to one or both of the driver and the skin surface.

10. The angled intraosseous access system according to claim 1, wherein a portion of the guide plate is configured to abut against a portion of the needle assembly to prevent a distal tip of the needle from backwalling a far wall of the medullary cavity.

11. A method of accessing a medullary cavity, comprising:
   engaging a skin engaging surface of a guide plate with a skin surface;
   aligning a needle of an intraosseous access system with a channel of the guide plate, the channel extending at a predetermined angle relative to the skin engaging surface;
   engaging a guide recess, disposed on the skin engaging surface, with an anatomical landmark body part;
   sliding a first portion of the guide plate including the guide recess disposed thereon, relative to a second portion of the guide plate including the channel, to align the needle with a target location; and
   advancing the needle through the channel to access the medullary cavity at the predetermined angle.

12. The method according to claim 11, wherein the predetermined angle is between 1°-90° relative to a longitudinal axis of the medullary cavity.

13. The method according to claim 11, wherein the skin engaging surface includes a concave or a convex portion configured to engage the skin surface.

14. The method according to claim 11, further including coupling the guide plate with a guide block configured to engage the skin surface and a driver of the intraosseous access system and maintain an axis of the driver at the predetermined angle.

15. The method according to claim 11, wherein the predetermined angle is less than or equal to 45°.

16. The method according to claim 11, further including adhering a portion of the guide plate to one of a driver or the skin surface.

17. The method according to claim 11, further including abutting a portion of a needle hub, coupled to the needle against a surface of the guide plate to prevent a distal tip of the needle from backwalling a far wall of the medullary cavity.

18. A method of accessing a medullary cavity, comprising:
   engaging a portion of a driver of an intraosseous access system with a surface of a guide block, the driver including a needle;
   engaging a skin engaging surface of the guide block with a skin surface; aligning an axis of the needle of the intraosseous access system with a predetermined angle; engaging the portion of the driver with a first series of notches to align the axis of the needle with a first predetermined angle or engaging the portion of the driver with a second series of notches to align the axis of the needle with a second predetermined angle different from the first predetermined angle; and
   advancing the needle along the needle axis to access the medullary cavity at the predetermined angle.

19. The method according to claim 18, wherein the predetermined angle is between 1°-90° relative to a longitudinal axis of the medullary cavity.

20. The method according to claim 18, further including engaging a guide recess disposed on the skin engaging surface with an anatomical landmark body part to align the needle with a target location.

21. The method according to claim 20, further including sliding a first portion of the guide block including the guide recess disposed thereon, relative to a second portion of the guide block to align the needle with the target location.

22. The method according to claim 18, wherein the first predetermined angle is less than 90° and wherein the second predetermined angle is less than 45°.

* * * * *